US006174838B1

(12) United States Patent
Dahmen et al.

(10) Patent No.: US 6,174,838 B1
(45) Date of Patent: Jan. 16, 2001

(54) HERBICIDES BASED ON 4-BROMO-1-METHYL-5-TRIFLUOROMETHYL-3-(2-FLUORO-4-CHLORO-5-ISOPROXYCARBONYLPHENYL)PYRAZOLE

(75) Inventors: Peter Dahmen, Neuss; Dieter Feucht; Otto Schallner, both of Monheim, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/242,873

(22) PCT Filed: Aug. 18, 1997

(86) PCT No.: PCT/EP97/04496

§ 371 Date: Feb. 25, 1999

§ 102(e) Date: Feb. 25, 1999

(87) PCT Pub. No.: WO98/08383

PCT Pub. Date: Mar. 5, 1998

(30) Foreign Application Priority Data

Aug. 28, 1996 (DE) ............................................... 196 34 701

(51) Int. Cl.⁷ .......................... A01N 43/56; A01N 43/824
(52) U.S. Cl. .............................................................. 504/139
(58) Field of Search ............................................... 504/139

(56) References Cited

U.S. PATENT DOCUMENTS

| 4,968,342 | 11/1990 | Forster et al. | 71/90 |
|---|---|---|---|
| 5,032,165 | 7/1991 | Miura et al. | 71/92 |
| 5,090,991 | 2/1992 | Forster et al. | 71/90 |
| 5,281,571 | 1/1994 | Woodard et al. | 504/225 |
| 5,587,485 | 12/1996 | Chupp et al. | 548/377.1 |
| 5,635,448 | 6/1997 | Mabuchi et al. | 504/139 |
| 5,686,386 | 11/1997 | Mabuchi et al. | 504/128 |

FOREIGN PATENT DOCUMENTS

| 2165743 | 6/1996 | (CA) . |
| 3-163063 | 7/1991 | (JP) . |

OTHER PUBLICATIONS

S.R. Colby, "Calculating Synergistic and Antagonistic Responses of Herbicide Combinations", Weeds, 15, pp. 20–22.

*Primary Examiner*—S. Mark Clardy
(74) *Attorney, Agent, or Firm*—Joseph C. Gil

(57) ABSTRACT

The present invention relates to novel herbicidal, synergistic compositions based on 4-bromo-1-methyl-5-trifluoromethyl-3-(2-fluoro-4-chloro-5-isopropoxy-carbonyl-phenyl)pyrazole and heteroaryloxyacetamides.

4 Claims, No Drawings

HERBICIDES BASED ON 4-BROMO-1-METHYL-5-TRIFLUOROMETHYL-3-(2-FLUORO-4-CHLORO-5-ISOPROXYCARBONYLPHENYL)PYRAZOLE

This application has been filed under 35 USC 371 as the national stage of international application PCT/EP97/04496, filed Aug. 18, 1997.

TECHNICAL FIELD OF THE INVENTION

The object of the present application was to provide a novel synergistic herbicidal active compound combination based on a novel active compound from the class of 3-phenylpyrazoles and an active compound from the class of heteroaryloxyacetamides having a pronounced action against both monocotyledon and dicotyledon weeds.

BACKGROUND OF THE INVENTION

Both the class of 3-phenylpyrazoles and the class of heteroaryloxyacetamides have been widely investigated in respect of their herbicidal activity.

EP 361 114 describes 3-(4-chlorophenyl)pyrazoles generally as herbicides for control of the most diverse weeds by the pre-emergence method and by the post-emergence method, in particular in rice crops.

JP 03 163 063 also describes the use of 3-substituted phenylpyrazoles for herbicidal use in agriculture.

Finally, 3-substituted phenylpyrazoles for herbicidal use are also described in U.S. Pat. No. 5,281,571. Possible mixing partners are also mentioned in this specification, inter alia 2-chloro-N,N-dialkylacetamide, N,N-dimethyl-2,2-diphenylacetamide, N-(2,4-dimethylthien-3-yl)-N-(1-methoxyprop-2-yl)-2-chloroacetamide, N-(1H-pyrazol-1-ylmethyl-N-(2,4-dimethylthien-3-yl)-2-chloroacetamide, N-(1-pyrazol-1-yl-methyl)-N-(4,6-dimethoxypyrimidin-5-yl)-2-chloroacetamide and N-(2,4-dimethyl-5-[[[(trifluoromethyl)sulfonyl]amino]-phenyl]acetamide. However, no mixture with an acetamide herbicide and a defined 3-phenylpyrazole is described.

DETAILED DESCRIPTION OF THE INVENTION

Surprisingly, it has now been found in biological tests, and therein lies the achievement of the object, that 4-bromo-1-methyl-5-trifluoromethyl-3-(2-fluoro-4-chloro-5-isopropoxycarbonylphenylpyrazole of the formula (I)

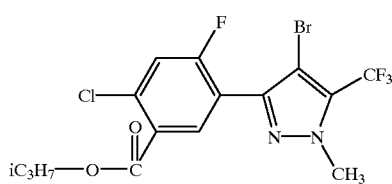

both by itself and in a mixture with a herbicide from the class of heteroaryloxyacetamides, when used together, shows decidedly synergistic properties in respect of the effectiveness against weeds. The active compound can be used particularly advantageously, by itself or as a broad-action combination preparation, for selectively combating weeds—both monocotyledon and dicotyledon weeds, by the pre-emergence and post-emergence method—in monocotyledon and dicotyledon crops of useful plants, such as, for example, maize, wheat, barley, rice, soya and cotton, a number of economically important (problem) broad-leaved weeds and gramineous weeds being reliably controlled thereby.

The present invention relates to herbicidal, synergistic compositions, characterized by an active content of an active compound combination comprising 4-bromo-1-methyl-5-trifluoromethyl-3-(2-fluoro-4-chloro-5-isopropoxy-carbonylphenyl)pyrazole of the formula (I)

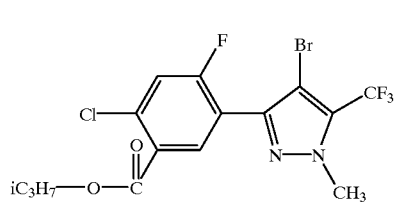

and an active compound of the formula (II)

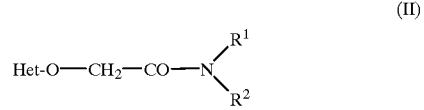

wherein
Het represents an optionally substituted heteroaromatic radical from the series consisting of 1,3-thiazol-2-yl, 1,2,4-thiadiazol-2-yl, 1,3,4-thiadiazol-2-yl, benzoxazol-2-yl and benzothiazol-2-yl,
$R^1$ represents in each case optionally substituted $C_1$–$C_4$-alkyl, $C_3$–$C_4$-alkenyl or $C_3$–$C_4$-alkoxy and
$R^2$ represents in each case optionally substituted $C_1$–$C_4$-alkyl, $C_3$–$C_4$-alkenyl or phenyl.

Herbicidal compositions according to the invention of the compound of the abovementioned formula (I) with (5-trifluoromethyl-1,3,4-thiadiazol-2-yl-oxy)-acetic acid N-isopropyl-N-(4-fluorophenyl) amide of the formula (II-1)

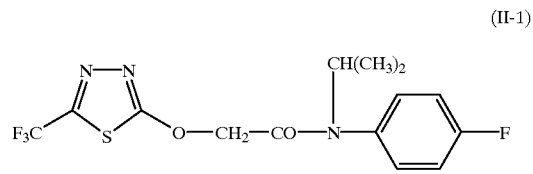

are particularly preferred.

The compound of the formula (11-1) is known, for example from EP-A 348 737 and U.S. Pat. No. 4,968,342

The heteroaryloxyacetamides defined under group (II) preferably act against monocotyledon weeds (=gramineous weeds). However, they also additionally act against some dicotyledon weeds.

It has now been found, surprisingly, that the active compound combinations defined above, from the heteroaryloxyacetamides of the formula (II) and 4-bromo-1-methyl-5-trifluoromethyl-3-(2-fluoro-4-chloro-5-isopropoxycarbonylphenyl)pyrazole have a particularly high activity and can be used selectively in many crops.

Surprisingly, the herbicidal activity of the active compound combination according to the invention is considerably higher than the sum of the actions of the individual active compounds.

An unforeseeable true synergistic effect thus exists, and not merely a supplementary action. The novel active compound combinations are readily tolerated in many crops, weeds which are otherwise difficult to control, such as Galium aparine and Lolium species, also being controlled well by the novel active compound combinations. The novel active compound combinations thus represent a valuable enrichment of selective herbicides.

The active compound combinations according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

The synergistic effect of the active compound combinations according to the invention is particularly highly pronounced at certain concentration ratios. However, the weight ratios of the active compounds in the active compound combinations can be varied within relatively wide ranges. In general, 0.001 to 1000 parts by weight preferably 0.01 to 100 parts by weight and particularly preferably 0.1 to 30 parts by weight, of active compound of the formula (II) are present per 1 part by weight of active compound of the formula (I).

The active compounds or active compound combinations can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth and ground synthetic minerals, such as highly disperse silica, alumina and silicates, as solid carriers for granules there are suitable. for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight of active compound combination, preferably between 0.5 and 90%.

The active compound combinations according to the invention are in general used in the form of finished formulations. However, the active compounds contained in the active compound combinations can also be mixed in individual formulations when used, i.e. used in the form of tank mixes.

The novel active compound combinations, as such or in their formulations, can furthermore also be used as a mixture with other known herbicides, finished formulations or tank mixes again being possible. A mixture with other known active compounds, such as fungicides, insecticides, acaricides, nematicides, bird repellents, growth factors, plant nutrients and agents which improve soil structure, is also possible. For certain intended uses, in particular in the post-emergence method, it may furthermore be advantageous to include, as further additives in the formulations, mineral or vegetable oils which are tolerated by plants (for example the commercial preparation "Oleo Dupont 11E"), or ammonium salts such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. They are used in the customary manner, for example by watering, spraying, atomizing, dusting or scattering.

The amounts of the active compound combinations according to the invention applied can be varied within a certain range; they depend, inter alia, on the weather and on soil factors. In general, the amounts applied are between 0.01 and 10 kg per ha, preferably between 0.05 and 5 kg per ha, particularly preferably between 0.1 and 3.0 kg per ha.

The active compound combinations according to the invention can be applied before and after emergence of the plants, that is to say by the pre-emergence and post-emergence method.

The good herbicidal action of the novel active compound combinations can be seen from the following examples. While the individual active compounds show weaknesses in herbicidal action, the combinations all show a very good action on weeds which goes beyond simple summation of the action.

A synergistic effect always exists in herbicides if the herbicidal action of the active compound combination is greater than that of the individual active compounds applied.

The action to be expected for a given combination of two herbicides can be calculated as follows (cf. COLBY, S. R.: "Calculating synergistic and antagonistic responses of herbicide combinations", Weeds 15, pages 20–22, 1967):

If X=% damage by herbicide A (active compound of group 1) when applied in an amount of p kg/ha and Y=% damage by herbicide B (active compound of group 2) when applied in an amount of p kg/ha and E=the expected damage of herbicides A and B when applied in an amount of p and q kg/ha, then $E = X + Y - (X \cdot Y/100)$.

If the actual damage is greater than that calculated, the combination is super-additive in its action, i.e. it shows a synergistic effect.

The following examples show that the herbicidal action found for the active compound combinations according to the invention on weeds is greater than that calculated, i.e. that the novel active compound combinations act synergistically.

USE EXAMPLES

To prepare the active compound preparations required for the experiments, corresponding amounts of a water-dispersible powder formulation (WP) of the heteroaryloxyacetamide of the formula (II-1) and in each case a commercially available formulation of the active compound of the formula (I) are weighed out and diluted with water to the desired concentration; various combinations of the two active compounds were prepared by mixing.

The tests were carried out as follows:

A) Pre-emergence tests/greenhouse

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After the treatment, the test plants are kept in a greenhouse under controlled conditions (temperature, atmospheric humidity, light) until they are evaluated. After 3 weeks, the degree of damage to the plants is rated in % damage in comparison with the development of untreated control plants.

The figures denote:

0%=no action/damage (like untreated control)

100%=total destruction

B) Post-emergence tests/greenhouse

Test plants which have a height of 5 to 15 cm are sprayed with the preparations of the active compound in such a way as to apply the particular amounts of active compound desired per unit area. The concentration of the spray liquors is so chosen that the particular amounts of active compound desired are applied in 500 l of water per ha. After the treatment, the test plants are kept in a greenhouse under controlled conditions (temperature, atmospheric humidity, light) until they are evaluated. After three weeks, the degree of damage to the plants is rated in % damage in comparison to the development of untreated control plants.

The figures denote:

0%=no action/damage (like untreated control)

100%=total destruction

The active compounds, amounts applied and results can each be seen from the following tables.

TABLE 1

Herbicidal action against Apera spica-venti by (I), (II-1) and a tank mix of (I) and (II-1) by the pre-emergence method

| Preparation | Dosage g of a.i./ha | Herbicidal action in % Apera spica-venti |
|---|---|---|
| (II-1) | 30 | 50 |
| (II-1) | 15 | 50 |
| (I) | 60 | 80 |
| (I) | 30 | 80 |
| (I) | 15 | 20 |
| (I) | 8 | 0 |
| (II-1) +(I) | 30 +60 | 100 |
| (II-1) +(I) | 15 +60 | 100 |
| (II-1) +(I) | 30 +30 | 100 |
| (II-1) +(I) | 15 +30 | 100 |
| (II-1) +(I) | 30 +15 | 100 |
| (II-1) +(I) | 15 +15 | 100 |
| (II-1) +(I) | 30 +8 | 100 |
| (II-1) +(I) | 15 +8 | 98 |

TABLE 2

Herbicidal action against Stellaria media by (I), (II-1) and a tank mix of (I) and (II-1) by the post-emergence method

| Preparation | Dosage g of a.i./ha | Herbicidal action in % Stellaria media |
|---|---|---|
| (II-1) | 125 | 0 |
| (II-1) | 60 | 0 |
| (I) | 15 | 80 |
| (I) | 8 | 60 |
| (II-1) +(I) | 125 +15 | 100 |
| (II-1) +(I) | 125 +8 | 80 |
| (II-1) +(I) | 60 +15 | 98 |
| (II-1) +(I) | 60 +8 | 80 |

What is claimed is:

1. A herbicidal composition comprising an active content of an active compound combination comprising 4-bromo-1-methyl-5-trifluoromethyl-3-(2-fluoro-4-chloro-5-isopropoxycarbonylphenyl)pyrazole and (5-trifluoromethyl-1,3,4-thiadiazol-2-yl-oxy)acetic acid N-isopropyl-N-(4-fluoro-phenyl)amide.

2. A method of controlling weeds, comprising the step of applying a herbicidal composition according to claim 1, to the weeds and/or their habitat by the pre-emergence method and/or by the post-emergence method.

3. A herbicidal composition according to claim 1, comprising from 0.001 to 1000 parts by weight of (5-trifluoromethyl-1,3,4-thiadiazol-2-yl-oxy)-acetic acid N-isopropyl-N-(4-fluoro-phenyl)amide per part by weight of 4-bromo-1-methyl-5-trifluoromethyl-3-(2-fluoro-4-chloro-5-isopropoxy-carbonylphenyl)pyrazole.

4. A herbicidal composition according to claim 1, comprising between 0.1 and 95% by weight of the active compound combination.

* * * * *